(12) United States Patent
Hilton (10) Patent No.: US 10,695,214 B2
(45) Date of Patent: Jun. 30, 2020

(54) PROTECTIVE CLOTHING AND APPAREL FOR PETS AND ANIMALS AND METHOD OF USE

(76) Inventor: Teresa Hilton, Vero Beach, FL (US)

( * ) Notice: Subject to any disclaimer, the term of this patent is extended or adjusted under 35 U.S.C. 154(b) by 0 days.

(21) Appl. No.: 13/005,867

(22) Filed: Jan. 13, 2011

(65) Prior Publication Data

US 2013/0066409 A1 Mar. 14, 2013

Related U.S. Application Data

(60) Provisional application No. 61/319,784, filed on Mar. 31, 2010, provisional application No. 61/319,949, filed on Apr. 1, 2010.

(51) Int. Cl.
*A01K 13/00* (2006.01)
*A61F 7/02* (2006.01)
*A61F 7/00* (2006.01)

(52) U.S. Cl.
CPC .............. *A61F 7/02* (2013.01); *A01K 13/006* (2013.01); *A61F 2007/0008* (2013.01);
(Continued)

(58) Field of Classification Search
CPC ......... A01K 13/00; A01K 13/006; B68C 5/00
(Continued)

(56) References Cited

U.S. PATENT DOCUMENTS

| 120,208 A | 10/1871 | McGovern |
|---|---|---|
| 750,505 A | 1/1904 | Walther |

(Continued)

FOREIGN PATENT DOCUMENTS

| DE | 10213615 A1 * | 10/2003 | ............ A01K 13/00 |
|---|---|---|---|
| JP | 10113088 A * | 5/1998 | ............ A01K 13/00 |

(Continued)

OTHER PUBLICATIONS

Machine translation of DE10213615.*

(Continued)

*Primary Examiner* — Thanh Pham
(74) *Attorney, Agent, or Firm* — Margaret A. La Croix (57) ABSTRACT

Protective clothing and apparel for pets and animals, and method of using same, structured as a shirt and/or hat made of an ultraviolet protective rash guard material with at least on portion having cooling crystals integrated therein. In a first embodiment the clothing is directed to a pet shirt constructed having a top portion, bottom portion, and side portions arranged to form a generally tubular member having an opened torso end, two leg members, and a collar member. In a second embodiment the clothing is directed to a pet hat constructed having a top portion, side portions and a front portion having a visor member attached thereto, the side portions having a lower rim. Two ear members and securement means are integrated within the lower rim of the side portions. At least a portion of the shirt/hat comprises ultraviolet properties. Additionally, at least a portion of the shirt/hat comprises a cooling zone formed of a plurality of cooling crystals. Owing to the ultraviolet material and cooling crystals the pet clothing shields pets/dogs from harmful ultraviolet rays while keeping them cool and comfortable and mitigating heat exhaustion.

6 Claims, 11 Drawing Sheets

(52) U.S. Cl.
CPC ................. *A61F 2007/0024* (2013.01); *A61F 2007/0214* (2013.01); *A61F 2007/0233* (2013.01)

(58) Field of Classification Search
USPC ....... 119/855, 850, 856; 54/79.1, 79.2, 79.3, 54/79.4
See application file for complete search history.

(56) References Cited

U.S. PATENT DOCUMENTS

| | | | |
|---|---|---|---|
| 3,141,443 A | 7/1964 | Huey | |
| 4,451,934 A * | 6/1984 | Gioello | A41B 9/00 2/113 |
| 4,854,319 A | 8/1989 | Tobin | 128/380 |
| 4,969,317 A | 11/1990 | Ode | 54/80 |
| D313,676 S | 1/1991 | Indursky et al. | D30/145 |
| 5,060,458 A | 10/1991 | Curtis | 54/79 |
| 5,163,272 A | 11/1992 | Finley et al. | 54/80.1 |
| 5,537,954 A | 7/1996 | Beeghly et al. | 119/850 |
| 5,572,745 A | 11/1996 | Mainus | 2/171.2 |
| D404,851 S | 1/1999 | Braun | D30/145 |
| 5,996,537 A | 12/1999 | Caditz | 119/850 |
| 6,085,698 A | 7/2000 | Klein | 119/859 |
| 6,089,194 A | 7/2000 | Labelle | 119/850 |
| 6,276,155 B2 * | 8/2001 | Siman-Tov | A41D 13/0056 165/46 |
| 7,043,765 B1 * | 5/2006 | Otsubo | A41B 1/00 2/115 |
| D539,488 S | 3/2007 | Phillips et al. | D30/145 |
| 8,585,746 B2 * | 11/2013 | Ilcheva | A41D 13/0518 607/108 |
| 2005/0246826 A1 * | 11/2005 | McCarter | A41D 13/0053 2/458 |
| 2005/0284416 A1 | 12/2005 | Smit et al. | 119/850 |
| 2006/0213156 A1 * | 9/2006 | Nilfuroshan | 54/79.1 |
| 2007/0193532 A1 | 8/2007 | Shelton | 119/850 |
| 2008/0040839 A1 | 2/2008 | Gordon | 2/455 |
| 2008/0067163 A1 | 3/2008 | Axinte et al. | 219/211 |
| 2008/0077214 A1 | 3/2008 | Stalick | 607/112 |
| 2008/0110414 A1 * | 5/2008 | Buehner | 119/712 |
| 2008/0163831 A1 | 7/2008 | Romanuck | 119/850 |
| 2012/0291175 A1 * | 11/2012 | Lawrence | A41D 27/136 2/53 |

FOREIGN PATENT DOCUMENTS

| | | | |
|---|---|---|---|
| JP | 2004049208 | 2/2004 | ............. A01K 13/00 |
| JP | 2007282577 | 11/2007 | ............. A01K 13/00 |

OTHER PUBLICATIONS

"MiraCool Cooling Crystals" at http://www.tuffrhino.com/MiraCool_s/45.htm.
"Cooling Caps, Hats, Do Rags, and Neck Tie Bandanas" at http://www.tearcatcher.com/hats.html.
"Pet Rash Guard" at http://www.bodyglove.com/store/products_detail.php?product_id=35319.
"UV Protection Clothing for Dog" at http://www.tugasunwear.com/uv_protection_clothing_dogs.html?osCsid=dnh5i4bpquafgt880jefrs2vf2.

* cited by examiner

PROTECTIVE CLOTHING AND APPAREL FOR PETS AND ANIMALS AND METHOD OF USE

CROSS-REFERENCE TO RELATED APPLICATIONS

This is a non-provisional patent application of provisional application U.S. Ser. Nos. 61/319,784, filed Mar. 31, 2010, and 61/319,949 filed Apr. 1, 2010, the disclosures of which are hereby incorporated in their entirety by reference thereto.

BACKGROUND OF THE INVENTION

1. Field of the Invention

The present invention relates to protective clothing and apparel for pets and animals and method of using same; particularly, the clothing is structured as a shirt and/or hat and is constructed with an ultraviolet protective rash guard material with at least on portion having cooling crystals integrated therein, wherein the clothing protects pets, particularly dogs, from ultraviolet rays and mitigates heat exposure.

2. Description of the Prior Art

Hot weather and/or direct sunlight can cause animals, particularly pets such as dogs, to overheat during outdoor activities. Heat exhaustion in dogs is not uncommon in hot weather. Early signs of heat exhaustion include heavy panting, hyperventilation, and increased salivation, weakness, and confusion or inattention. As the condition progresses towards heat stroke there may be obvious paleness or graying to the gums, shallow breathing, vomiting and diarrhea that may be bloody and finally seizures or coma. Even on moderately hot days an active dog can run the risk of heat exhaustion. What is more, sunlight is harmful to dogs owing to harmful ultraviolet rays penetrating the dog's eyes, as well as the risk of sun burn. Dogs, just like humans, can get sunburn. This is especially true for light coated short hair dogs. Particular breeds like Shar Peis, white Pit Bulls, and Chinese Crested Hairless dogs are especially susceptible. However, all dogs, even ones with thick coats, can get sunburn.

Various clothing articles have been proposed for animals and pets. Hats have been proposed for pets and animals. Examples of hats and/or sunshields heretofore disclosed and utilized include: U.S. Pat. Nos. 120,208; 4,969,317; 5,163,272; 750,505; D404,851; and D539,488. However, the problem with these hats is that they do not include ultraviolet fabric constructions and they fail to provide any type of internal cooling capabilities. What is more, many of the hats proposed are not suitable for long term wear by a canine, and do not include structural features to provide securement of the hat during activities.

Hats having cooling capabilities have been proposed for humans, but these hats are not structurally or functionally capable of being used for animals. Further, these hats fail to provide a pet hat that is lightweight with ultraviolet protective properties and optimal securement capabilities suitable for a canine's head to prevent the hat from loosening or falling off during high impact activities, such as running and playing. Examples of hats have cooling properties include: U.S. Pat. Nos. 4,854,319; and 5,572,745; and cooling caps, hats, do rags, and neck tie bandanas can be found at http://www.tearcatcher.com/hats.html. These proposed cooling hats are not structurally or functionally capable of acting as cooling wear for pets/dogs and would need major structural modification to be used for pets/dogs to withstand long term wear during strenuous pet activities.

An assortment of clothing articles have been proposed for animals and pets. Examples of dog covers/coats/boots heretofore disclosed and utilized include: U.S. Pat. Nos. 3,141,443; 5,060,458; 5,537,954; 6,089,194; 6,085,698; and D313,676; as well as U.S. Pat. App. Pub. Nos. 2007/0193532 and 2008/0067163; and 20080163831; foreign publications JP2004049208 and JP2007282577; pet rash guard to be worn by dogs can be found at http://www.bodyglove.com/store/products_detail.php?product_id=35319; UV protection clothing for dogs can be found at http://www.tugasunwear.com/uv_protection_clothing_dogs.html?osCsid=dnh5i4bpquafgt880jefrs2vf2. However, these dog covers/coats/boots generally provide protective coverings and fail to provide cooling capabilities. The problem many of the proposed covers/coats/boots for pets is concerned deals with keeping a dog/pet warm, rather than cool. Consequently, these articles generally provide insulation or heating capabilities rather than cooling capabilities.

Various clothing articles have been proposed that include cooling capabilities integrated within pet clothing. However these articles fail to provide a light weight pet clothing article that provides ultraviolet protection and optimal fit and securement on the pet. Examples of dog articles having cooling properties include: U.S. Pat. No. 5,996,537; U.S. Pat. App. Pub. Nos. 20050284416; 20080040839; and 20080077214; and pet bandana found at http://www.tuffrhino.com/MiraCool_s/45.htm. While these proposed articles include cooling capabilities, the articles fail in combination to provide ultraviolet protection in the form of ultraviolet material along the torso of the animal, optimal securement for wear during strenuous pet activities, and optimal cooling zones for optimizing the cooling effect on the pet.

There remains a need in the art for protective clothing and apparel for pets and animals, and method of using same, structured as a shirt and/or hat made of a lightweight rash guard material having ultraviolet protective properties. There is a further need in the art for protective clothing for pets with cooling crystals integrated therein.

SUMMARY OF THE INVENTION

The present invention is directed to novel pet wear and/or improved pet wear that is composed of a lightweight rash guard material with ultraviolet protective properties and cooling crystals integrated therein. Advantageously, the ultraviolet material and cooling crystals shield the pet/dog from harmful ultraviolet rays while keeping them cool and comfortable and mitigating heat exhaustion.

In a first embodiment the article of clothing for a pet is directed to a pull-over shirt including a top portion, bottom portion, and side portions constructed to form a generally tubular member having an opened torso end. The tubular member is appointed to be slipped over the pet's/dog's torso. The tubular member includes two leg members integrated therein appointed to receive the legs of a dog/pet. A collar member is integrated within the tubular member for the dog's head to pass through. At least a portion of the tubular member comprises ultraviolet properties to protect the dog from ultraviolet rays. Additionally, at least a portion of the tubular member comprises a cooling zone. The cooling zone further being comprised of a plurality of polymeric cooling crystals formed in a cavity located within the tubular member.

In a second embodiment the article is directed to a hat for a pet. The hat is constructed having a top portion, side portions and a front portion having a visor member attached thereto, the side portions having a lower rim. Two ear members and securement means are integrated within the lower rim of the side portions. At least a portion of the hat comprises ultraviolet properties to protect the dog from ultraviolet rays. Additionally, at least a portion of the hat comprises a cooling zone. The cooling zone further being comprised of a plurality of cooling crystals formed in a cavity located within the hat.

A method of using cooling crystals integrated in clothing for animals is also provided in order to prevent/mitigate heat exhaustion. The method comprises the first step of placing an article of clothing for an animal in cold water for at least 30 minutes before wear to yield a soaked article. The article of clothing includes ultraviolet properties and at least one cooling zone comprised of a plurality of cooling crystals. As the article is soaked in water the cooling crystals absorb the water to provide a cooling structure to the article as it is worn. In the second broad step, the soaked article is placed on an animal, such as a dog, during warm weather to keep the animal cool. The method is directed to an article constructed as a shirt and hat.

BRIEF DESCRIPTION OF THE DRAWING

The invention will be more fully understood and further advantages will become apparent when reference is had to the following detailed description of the preferred embodiments of the invention and the accompanying drawings, in which:

FIG. 2b is a cross-sectional view taken along X-X of FIG. 2a;

FIG. 2c is a top planer view of the shirt shown in FIG. 1 and visa via FIG. 2a;

FIG. 5b illustrates a top view of the embodiment of FIG. 5a;

DETAILED DESCRIPTION OF THE INVENTION

This invention relates to novel pet wear and/or improved pet wear that is composed of a lightweight rash guard material with ultraviolet protective properties and cooling crystals integrated therein. The pet clothing and apparel, including a vest or shirt type garment and/or a hat or cap is constructed for pets, having particular applications for dogs, however general four legged pets are contemplated. The pet clothing and apparel is composed of lightweight material preferably imparted with UV protection properties. At least a portion of the pet clothing and apparel includes cooling crystals integrated therein. In a first embodiment, the pet clothing is formed as a shirt type garment preferably composed of a rash-guard material that is lining-free except preferably in regards to the areas where crystals are sewn into the clothing. Fabric forming the clothing is a UV/ultraviolet treated fabric, organic blend, and the shirt is formed as a one-piece "tubular" pullover. When formed a shirt, the articles simply slides over the pet's/dog's head and front legs and fits loosely around the chest, without restricting movement of the animal. In a second embodiment, the article is formed as a cap/pet baseball cap that is made of an air-wick material and includes tented elastic loopholes for pet ears to fit comfortably through. The cap further includes cooling crystals sewn into the cap, preferably in a crown area of the cap. Advantageously, the article of clothing is designed to shield pets/dogs from the harmful rays of the sun while keeping them cool and comfortable. Owing to the article's lightweight and breathable fabrics, pet owners can done the clothing onto the pet before going outside to prevent sunburn, dehydration, and heat stroke. The articles of clothing for pets are appointed to be available in a wide range of adorable colors and patterns and sized for pets/dogs of all sizes.

Fabric/or fabric combinations preferably used in the construction of the clothing of the subject invention include rash guard type materials. These materials include spandex, nylon or polyester material constructs, or combinations thereof. Rash guard materials are used for their light coverage in warm to extreme summer temperatures and are utilized for several watersports for preventing chaffing and offering some sun protection. Other important components of a rash guard include flatlock stitching, and six panel construction. Flatlock stitching creates a seam where the seam allowances lies flat to the garment instead of hanging loose from it. It is made by adjusting the overlock or the thread overedge stitch. Flatlock stitching increases the strength of the garment for intense exercise or recreational activities. Six panel construction versus the conventional four panel tee shirt construction enables the user increased mobility wet or dry. While rash guards have been utilized by surfers and athletes outdoors, rash guards have not been commonly utilized for pets, i.e. dogs. In particular, the use of the rash guard material allows a lightweight construction that further can be soaked in cold water to activate the cooling crystals without the shirt/hat material itself absorbing water and therefore providing a relatively dry shirt/hat to be worn without dripping or wetness.

Ultraviolet Protection Factor is integrated within the rash guard material to protect against the rays of the sun. Preferably, the textiles and fabrics employed in the use of the rash guard material are pre-treated with UV inhibiting ingredients during manufacture to enhance UV blocking capacity. Alternatively, wherein the fabrics and textiles utilized have inherent UV blocking properties based on fiber structure, density of weave, and dye components—especially darker colors and indigo dyes—pretreatment with UV inhibiting ingredients is not needed. Examples of lightweight synthetics fabrics preferably utilized in the construction of the pet clothing of the subject invention include polyester, nylon, Lycra and polypropylene.

Cooling crystals integrated into the construction of the article of clothing provide a cooling effect to further enhance the protective features of the clothing in preventing sunburn, dehydration and avoiding heat stroke. Polymeric cooling crystals are integrated into at least a portion of the protective pet clothing. Preferably, wherein the clothing is constructed as a rash guard protective shirt for a dog/pet, the cooling crystals are integrated within at least a portion of the underbelly of the shirt in order to expose the dog's chest directly to the cooling effect of the crystals. On at least the undercarriage of the shirt a cavity is formed wherein crystals are housed. Preferably, the top portion of the shirt also includes a cooling crystal zone so that the top of the torso also is cooled while the animal is outdoors. An outer layer, preferably composed of a lightweight absorbent cotton material covers the cavity housing the crystals. The shirt may be soaked in cold water for at least 30 minutes up to several hours before wear. As the shirt is soaked in cold water, the crystals swell up to many times their size and when the shirt is worn, the crystals provide a moist evaporative cooling for the pet. Advantageously, the shirt's cooling crystals can be re-cooled as needed and the shirt can be repeatedly worn.

The cooling zone preferably is constructed of a bottom layer and top layer forming a cavity housing a hydrophilic material, via the polymeric cooling crystals. The top outer layer is preferably composed of the rash guard material, as the rest of the shirt, for example. The bottom layer or inner layer is preferably constructed of a fibrous material adapted to absorb water. The cooling crystals are hydrophilic in nature and absorb water as it is soaked. Hydrophilic materials utilized as the cooling crystals have super absorbency properties. For example, the preferred material the hydrophilic material may include DT275 from Concert Industries Ltd., of Gatineau, Canada. During activation, the article is soaked in water for approximately 30 minutes whereby the cooling crystals and bottom layer/inner layer absorb water. The pet owner then wrings out the article to remove excess water. Owing to the rash guard material, the article itself does not retain much water and does not drip. The article is then donned onto the pet. Cooling effects achieved by the article can last between 2-3 hours at temperatures above 110 degrees Fahrenheit, and longer where the environmental temperature is lower.

Figure 1:
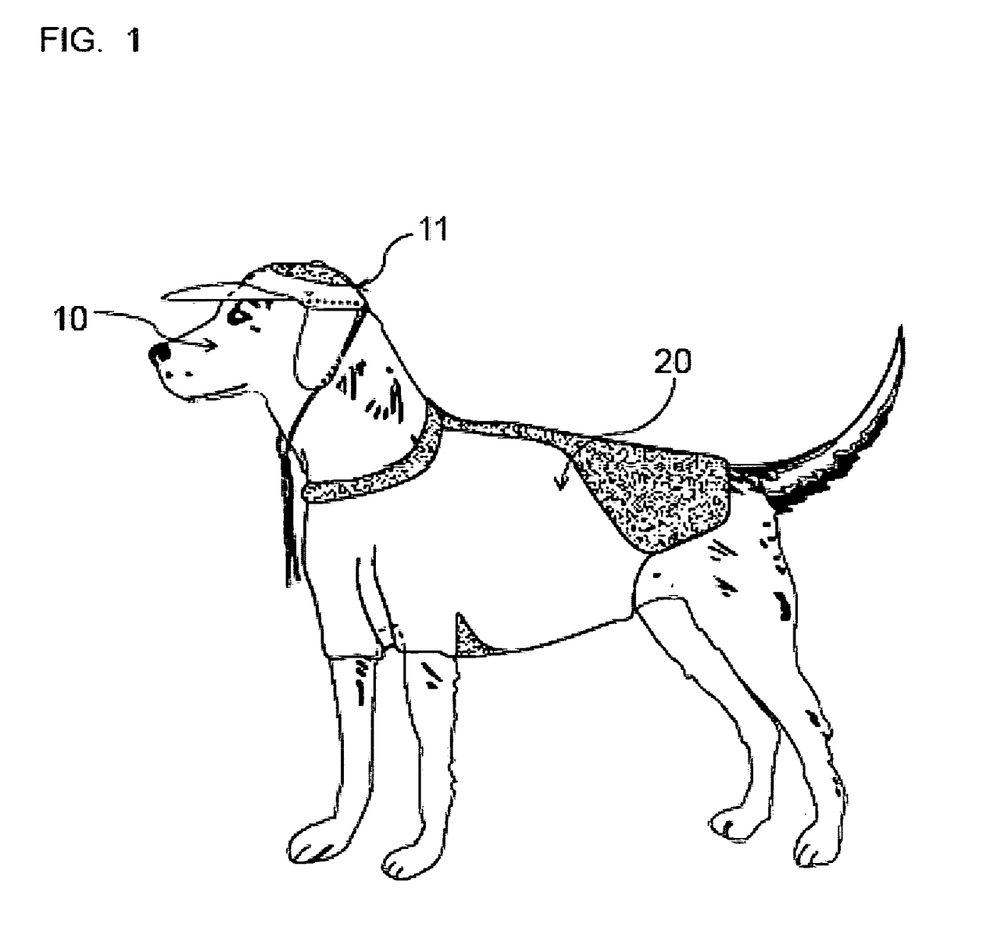
FIG. 1 illustrates a plane view of the article of clothing, showing a dog wearing a hat and a shirt constructed in accordance with the subject invention.
Figure 2A:
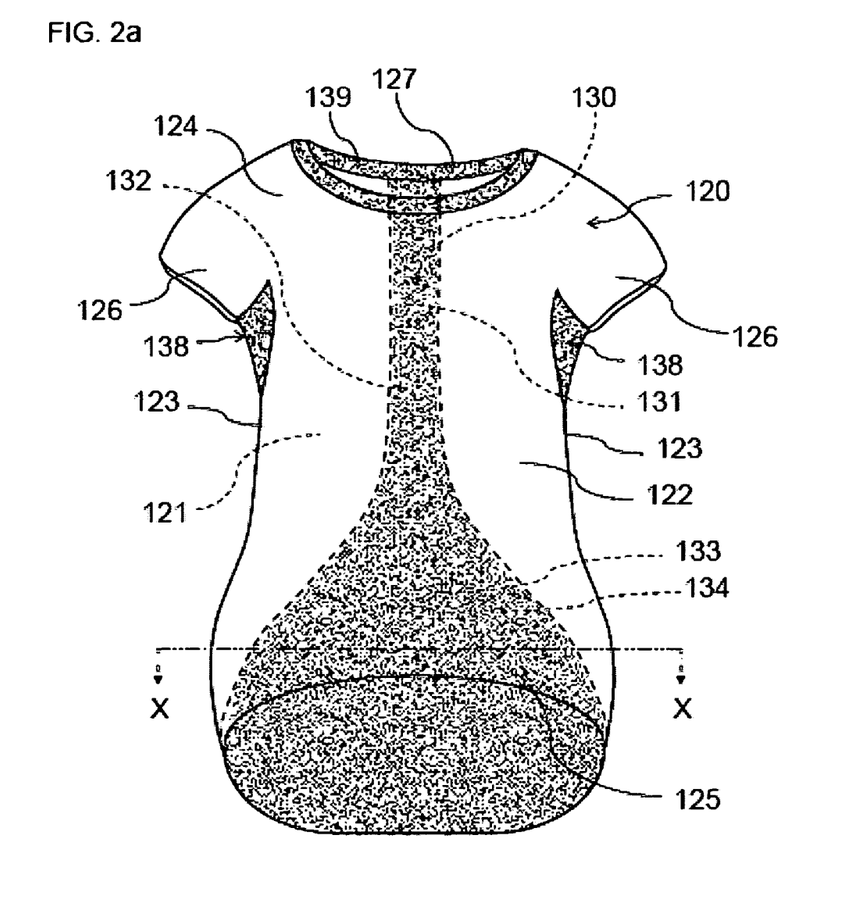
FIG. 2a is a bottom planer view of the shirt shown in FIG. 1.
Figure 2B:
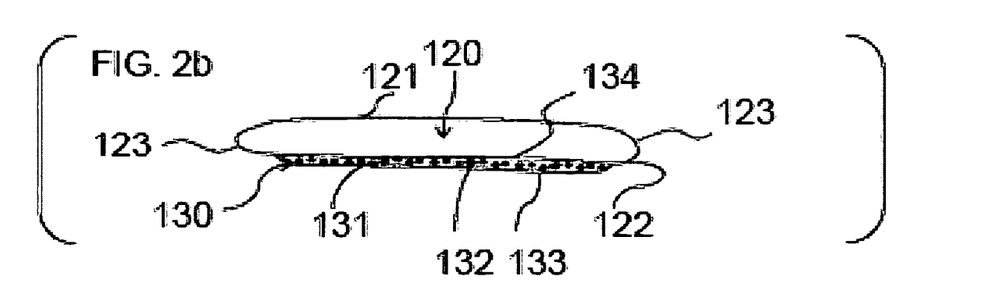
Figure 2C:
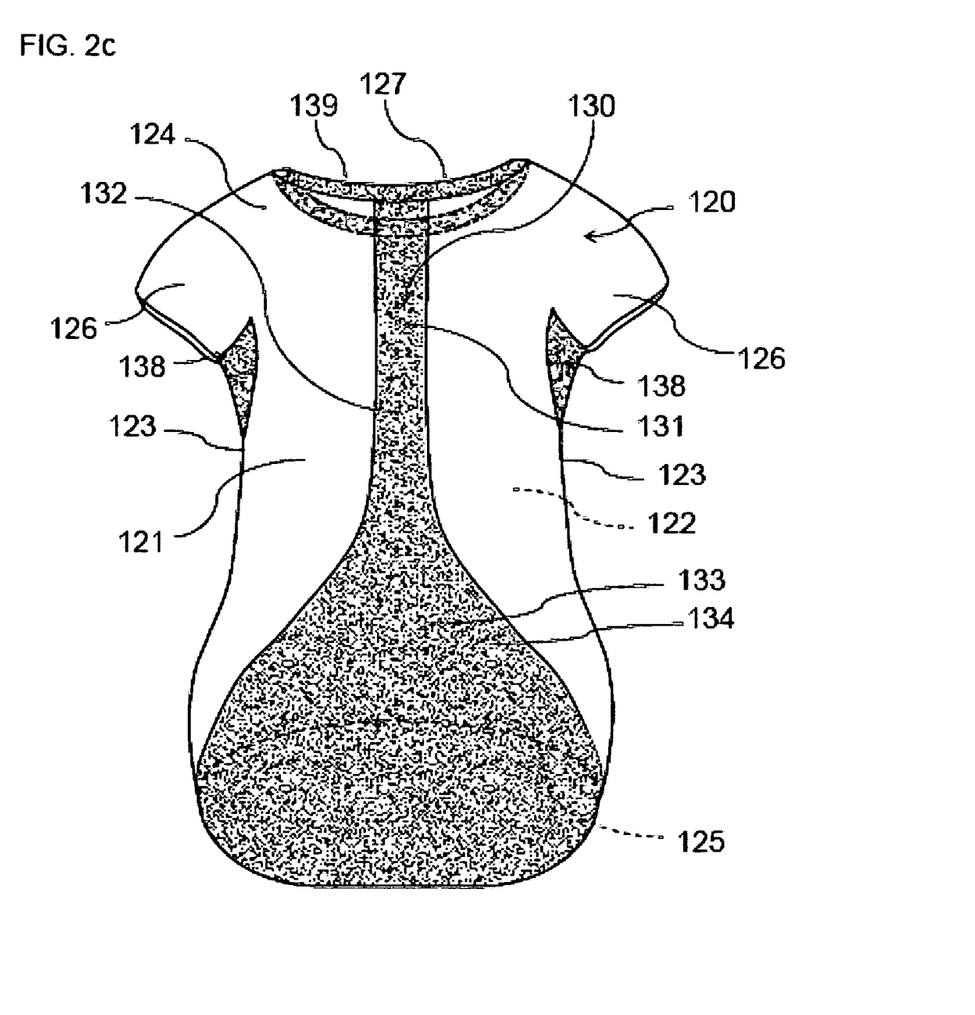

FIG. 1 illustrates a plane view of the article of clothing, showing a dog 10 wearing a hat 11 and a shirt 20 constructed in accordance with the subject invention. FIGS. 2a-2c are views of the shirt shown in FIG. 1. FIG. 2a is a bottom planer view; FIG. 2b is a cross-sectional view taken along X-X of FIG. 2a; and FIG. 2c is a top planer view.

Referring to FIG. 2a-2c, the article of clothing for a pet is constructed as a shirt 120. The shirt 120 includes a top portion 121, bottom portion 122, and side portions 123 constructed to form a generally tubular member 124 having an opened torso end 125. Two leg members 126 are integrated within the tubular member 124. A collar member 127 is integrated within the tubular member 124 located opposite from the opened torso end 125. At least a portion of the tubular member 124 comprises ultraviolet properties. Preferably, the entire shirt 120 includes UV properties/treatment. The shirt 120 is composed of fabric or/fabric combinations classified as rash guard type materials, including spandex, nylon, polyester, Lycra and polypropylene material constructs, or combinations thereof. The shirt 120 includes an ultraviolet protection factor integrated therein to protect against sun rays.

At least a portion of the tubular member 124 comprises a cooling zone 130. The cooling zone 130 further comprises a hydrophilic material 131 formed in a cavity 132 located within the tubular member 124. In the embodiment shown, the cooling zone 130 is constructed on the top portion 121 of the tubular member 124. A second cooling zone is preferably constructed along collar member 127 as shown at 139, and at the under-leg area as shown at 138 between the tubular member 124 and leg members 126. In this manner, the cooling effect is centralized to the under-leg area where the fur is thin and cooling can be affected in an optimal manner. Where thicker fur regions are provided it has been found to slow the heat transfer cooling effect and therefore decrease optimal cooling benefits.

Figure 3:
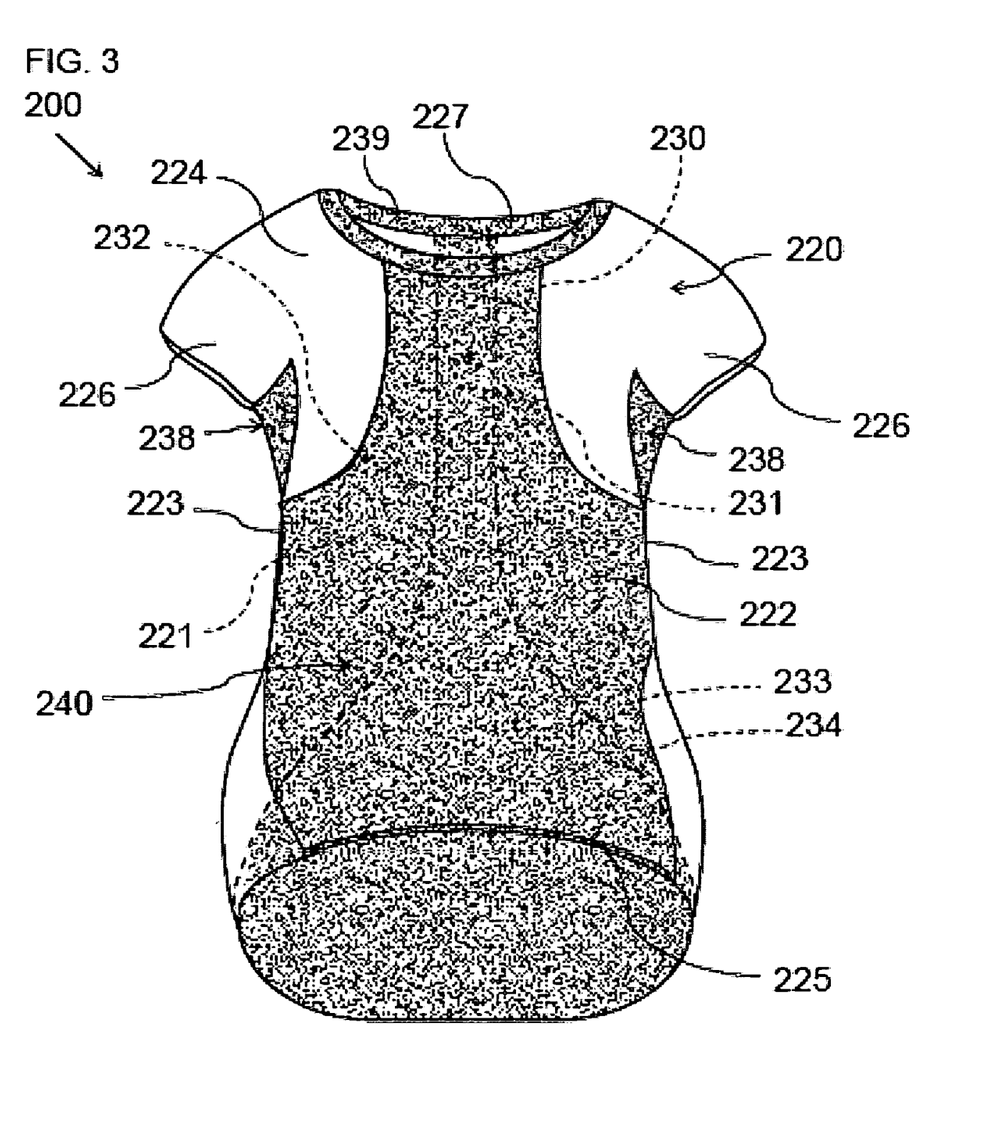
FIG. 3 is a bottom view of another embodiment of a shirt directed to the subject invention.

It has been found that particular placement of the cooling zones in areas where the fur of the dog is less dense provides for a more optimal cooling effect as the heat transfer has less fur interference. Therefore, although the cooling zone 130 is herein shown on the top portion 121 of the tubular member 124, the cooling zone is preferably located in addition to/or solely on the bottom portion 122 as shown in FIG. 3. That is because the underbelly of the animal/dog has low fur density in general as compared to the back of the animal, and consequently, heat transfer during cooling can be more effectively optimized at that region. There is preferably at least one cooling zone; preferably there is at least three cooling zones; however, there may be a plurality of cooling zones spaced throughout the article 120.

As best viewed in the cross-section view illustrated by FIG. 2b, the cooling zone 130 preferably includes an external layer 133 and a bottom layer 134 forming the internal cavity 132 containing hydrophilic material 131/cooling crystals. The bottom layer 134 preferably includes attachment means and is appointed to be removably attached to the tubular member 124 by way of the attachment means (not shown; representative of same can be found in FIG. 7a-7c). Preferably, the bottom layer 134/innermost layer (resting against the dog) of the cavity 132 is composed of an absorbent cotton material while the external layer 133/outer layer is composed of the rash guard material.

FIG. 3 is a bottom view of another embodiment of a shirt directed to the subject invention, shown generally at 200. The shirt 220 includes a top portion 221, bottom portion 222, and side portions 223 constructed to form a generally tubular member 224 having an opened torso end 225, leg members 226 and a collar member 227. At least a portion of the tubular member 224 comprises ultraviolet properties. At least a portion of the tubular member 224 comprises a cooling zone 230. The cooling zone 230 further comprises a hydrophilic material 231 formed in a cavity 232 located within the tubular member 224. In the embodiment shown, the cooling zone 230 is constructed on the top portion 221 of the tubular member 224, in the collar member 227 at 139, and at the under-leg area as shown at 228 between the tubular member 224 and leg members 226. Additionally, a cooling zone 240 is herein shown on the bottom portion 222 so that the low fur density underbelly of the dog is directly engaged for optimal cooling.

Figure 4A:
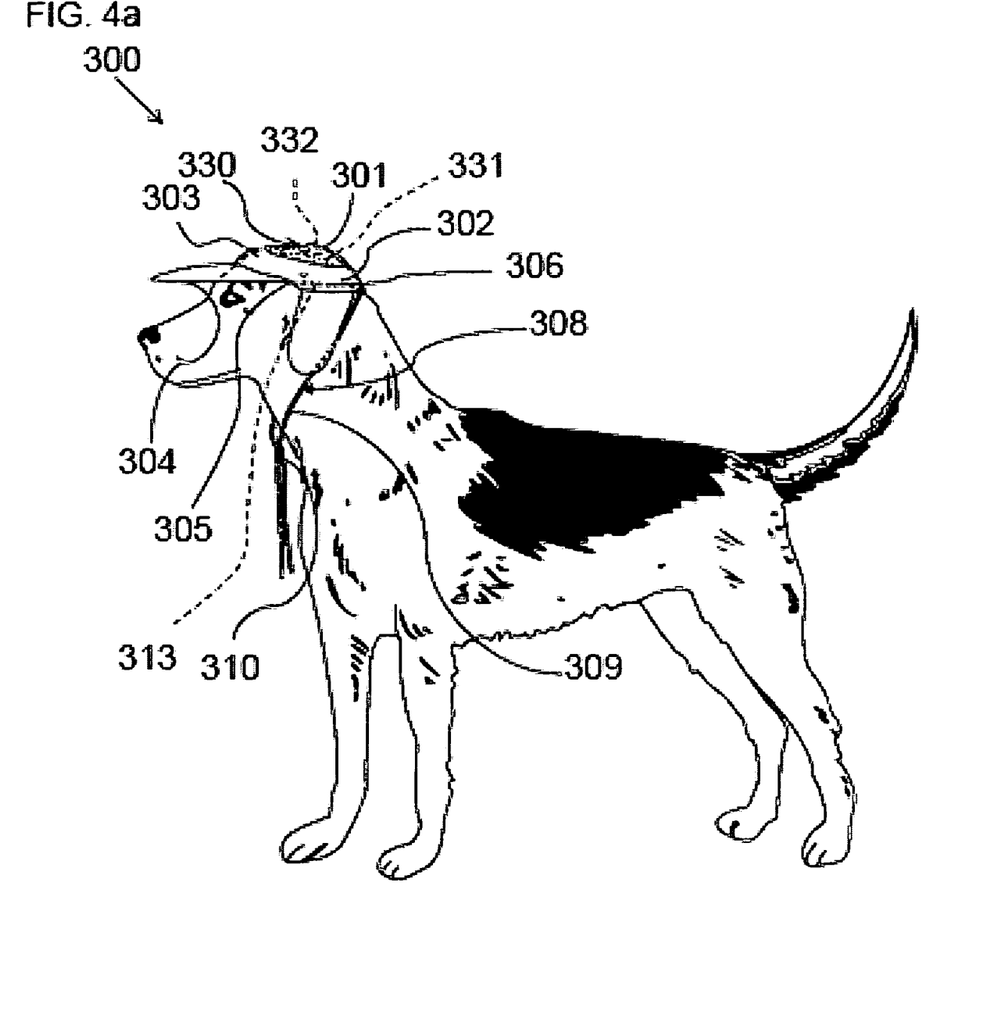
FIG. 4a illustrates a plane view of the article of clothing, showing a dog wearing a hat constructed in accordance with the subject invention.
Figure 4B:
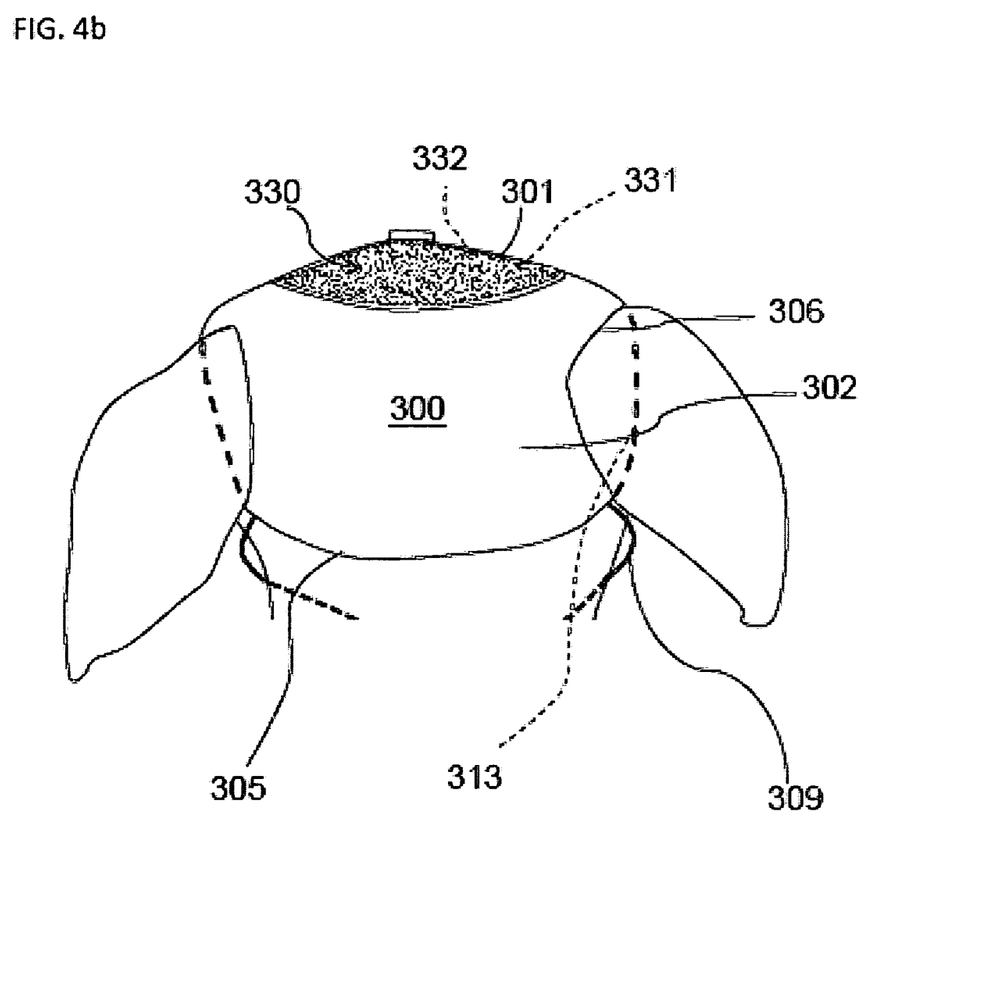
FIG. 4b illustrates a back view of the hat as worn on the dog.
Figure 4C:
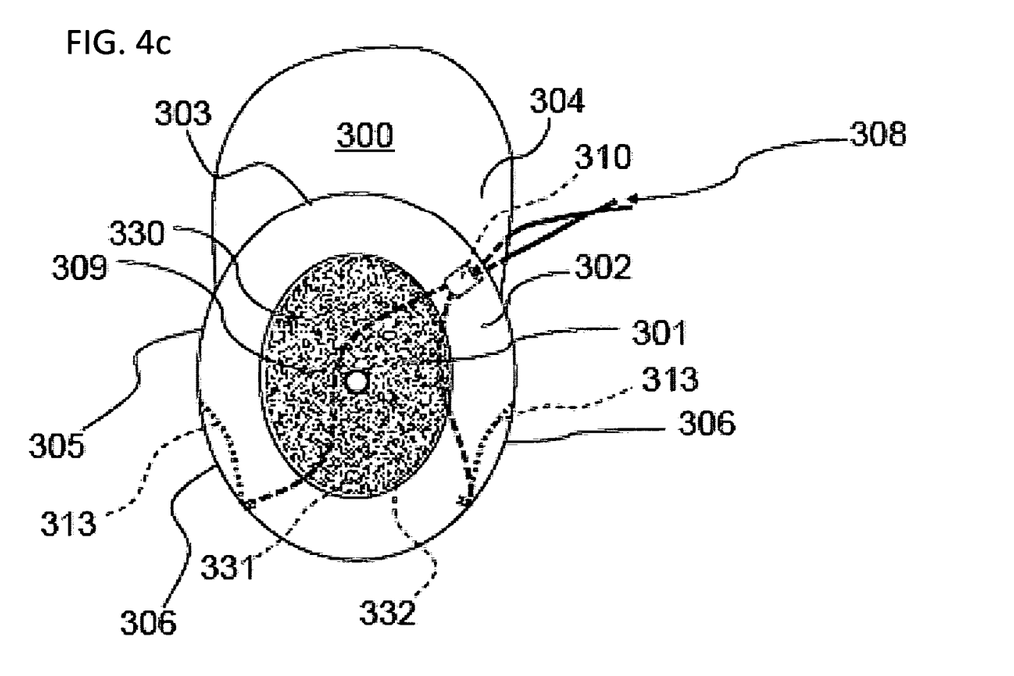
FIG. 4c illustrates a top view of the hat.
Figure 4D:
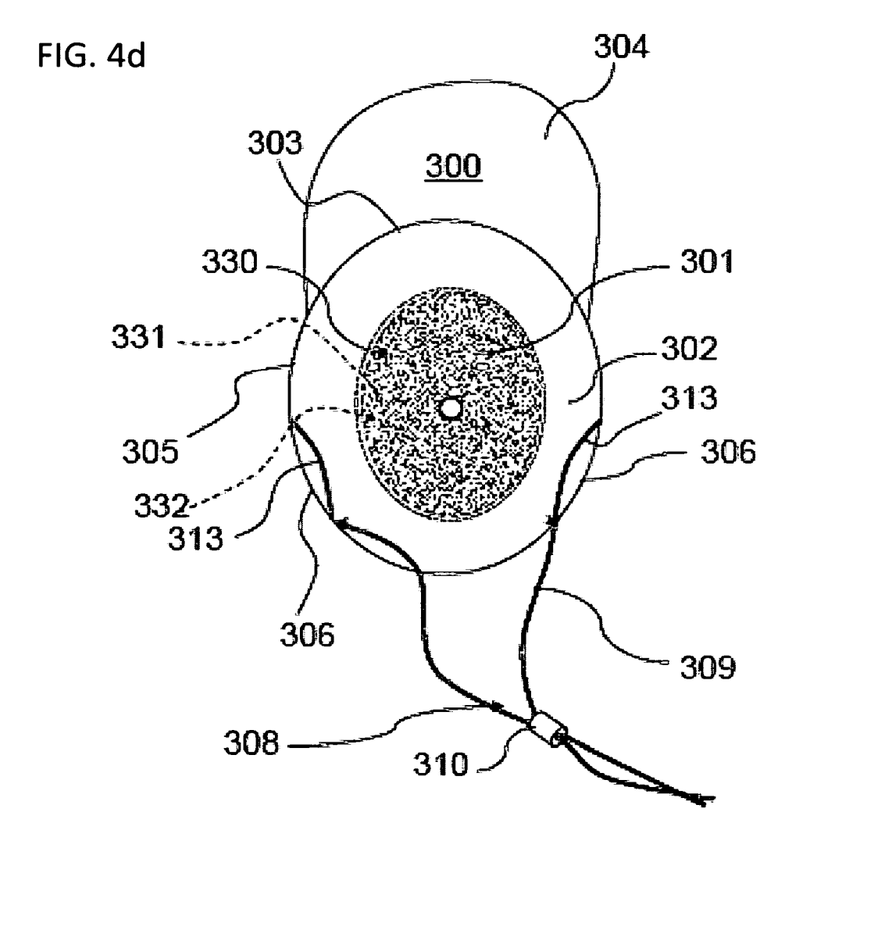
FIG. 4d illustrates a bottom view of the hat.

FIGS. 4a-4d illustrate plane views of the article of clothing directed to a dog/pet hat constructed in accordance with the subject invention. FIG. 4a illustrates a plane view; FIG. 4b illustrates a back view of the hat; FIG. 4c illustrates a top view of the hat; and FIG. 4d illustrates a bottom view of the hat. The hat for a pet is shown generally at 300. The hat 300 comprises a top portion 301, side portions 302 and a front portion 303 having a visor member 304 attached thereto. The side portions 302 have a lower rim 305 circumferentially surrounding the bottom of the hat 300. Securement means 308 is integrated within the side portions 302. Preferably the securement means 308 is constructed as a string or rope 309 with a toggle 310 discretely located under the lower rim 305 of the side portions 302 of the hat 300.

Additionally, two ear members 306 are integrated within the lower rim 305 of the side portions 302. The ear members 304 may come in at least two different embodiments, flush for dogs with substantially flat lying ears (i.e. like the Great Pyrenees breed) and aperture cut-out for dogs with substantially raised ears (i.e. like the German Shepherd breed). The flush version is herein shown in FIGS. 4a-4d, while the aperture cut-out version is shown in FIGS. 5a and 5b.

At least a portion of the hat comprises ultraviolet properties. Moreover, at least a portion of the hat 300 comprises a cooling zone 330. The cooling zone 330 further comprises of a plurality of cooling crystals/hydrophilic material 331 formed in a cavity 332 located within the hat 300. Preferably the cooling zone 330 is located within the lower rim 305 of the front portion 303 (as best illustrated by way of FIG. 6) because the fur located on the face region of the dog is thinner and more conducive to provide optimal heat transfer in cooling the dog. Alternatively the cooling zone is located within the lower rim 305 of the side portions 302 so that the cooling zone circumferentially surrounds the base/rim 303 of the hat. Further, alternatively, as in the embodiment shown, the cooling zone 330 is located within the top portion 301 of the hat. Further, in yet another embodiment, the ear members 304 include a securement band 313 appointed to slide under ears of an animal. The band 313 is preferably elastic in nature and flex to slide under the ears, which lay flat over the band 313, to hold the hat in place. Preferably the securement band 313 includes a cooling zone forming a cooling band (as shown in FIG. 6).

Figure 5A:
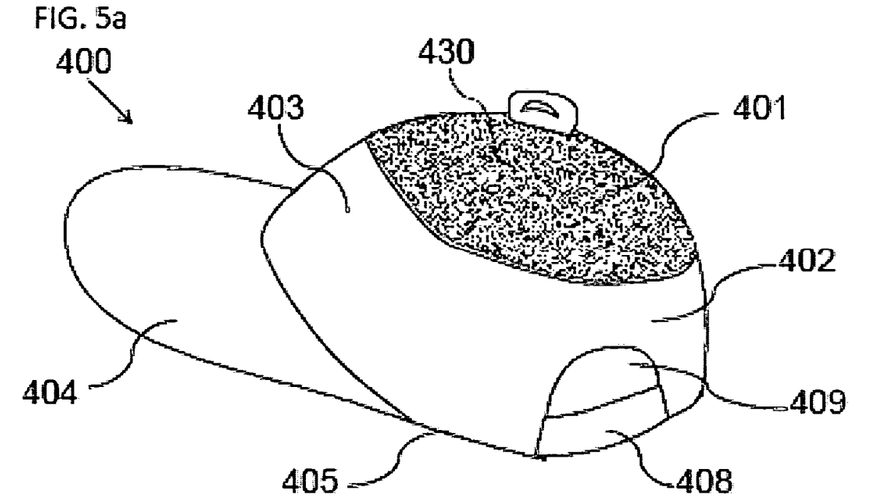
FIG. 5a illustrates a top side view of another embodiment of a hat constructed in accordance with the subject invention.
Figure 5B:
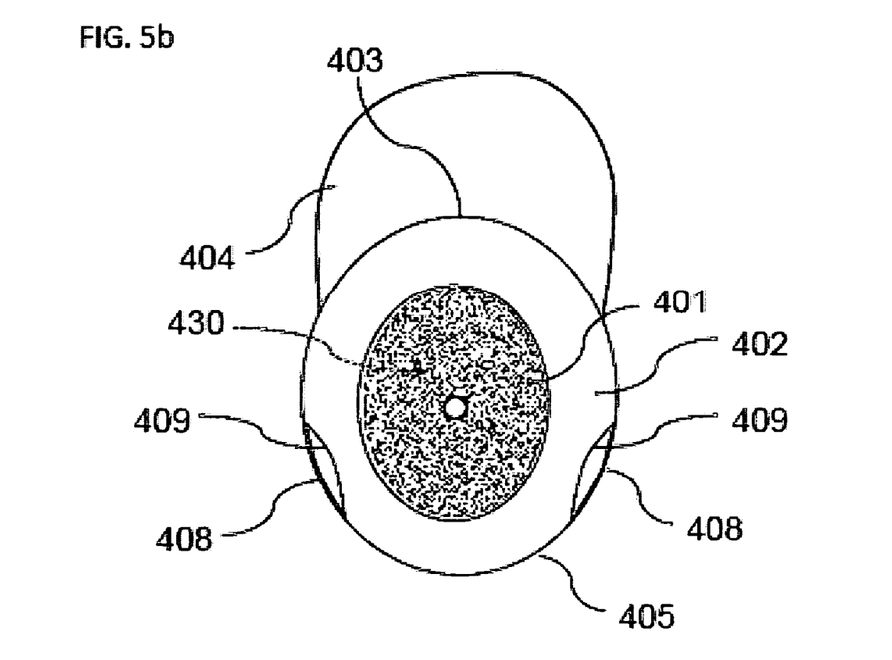

FIGS. 5a and 5b illustrate a top side view and top view, respectively, of another embodiment of a hat constructed in accordance with the subject invention, shown generally at 400. The hat 400 comprises a top portion 401, side portions 402 and a front portion 403 having a visor member 404 attached thereto. The side portions 402 have a lower rim 405 circumferentially surrounding the bottom of the hat 400. Securement means 408 is integrated within the side portions 402 by way of elastic bands. At least a portion of the hat comprises ultraviolet properties. Moreover, at least a portion of the hat comprises a cooling zone 430. Two ear members 409 are integrated within the lower rim 405 of the side portions 402. The ear members 409 are herein shown as aperture cut-outs for straight or substantially raised ears (i.e. like the German Shepherd breed) to pass through and stick out above the hat.

Figure 6:
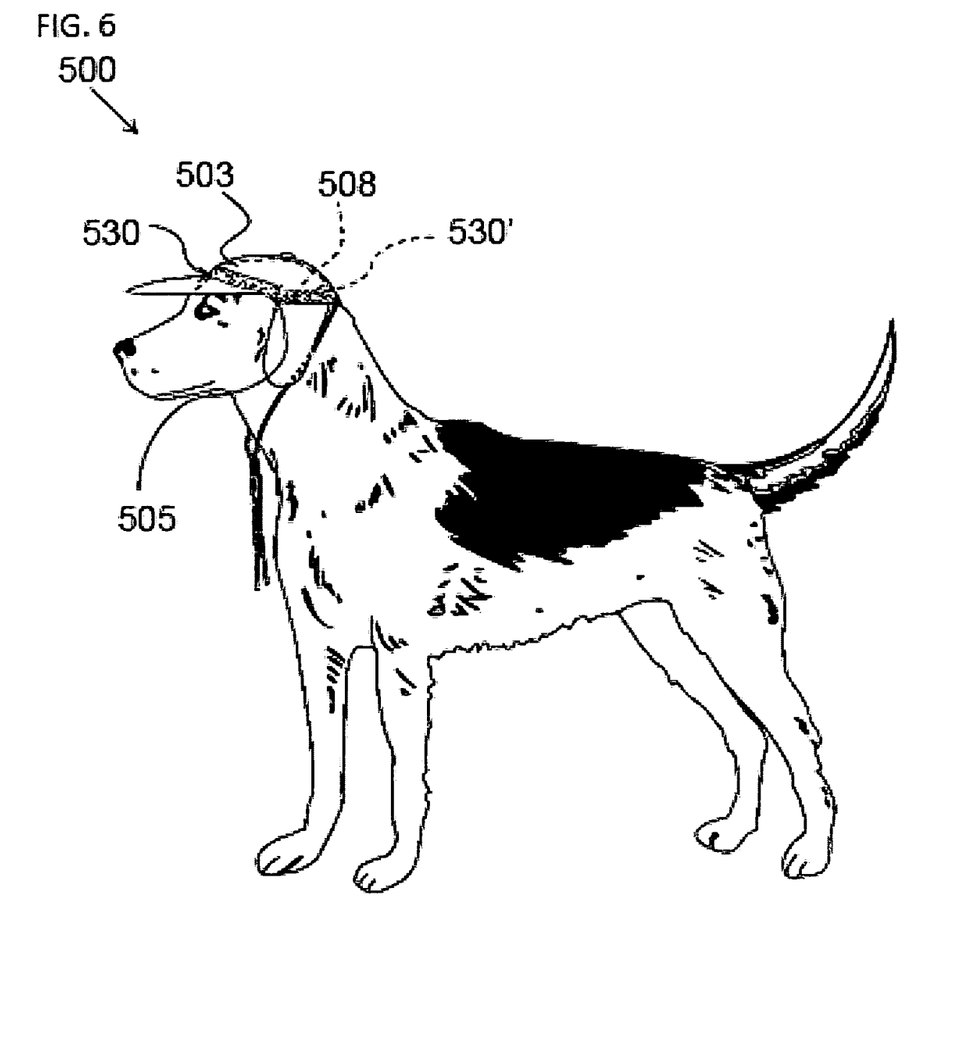
FIG. 6 illustrates a plane view of another embodiment of a hat constructed in accordance with the subject invention.

FIG. 6 illustrates a plane view of another embodiment of a hat constructed in accordance with the subject invention, shown generally at 500. In the embodiment shown, the cooling zones 530 and 530' are located within the lower rim 505 of the front portion 503 and in the securement bands 508. Because the securement bands 508 rest against the head of the animal near the face region wherein the fur is less dense, the cooling effect in this location provides optimal heat transfer and cooling. The same is true for the front portion 503 which has been found to be the most effective regions of treatment in cooling a dog down due to the fur being less dense in this region than on other regions of the dog's body. For example, it has been found that the top of the dog's coat and around the neck tend to be thickest, and therefore less penetrable in the cooling of the dog. On the other hand, less densely populated fur areas on the dog, such as the face, under the ears, ears, and underbelly tend to be more penetrable in the cooling effect.

Figure 7A:
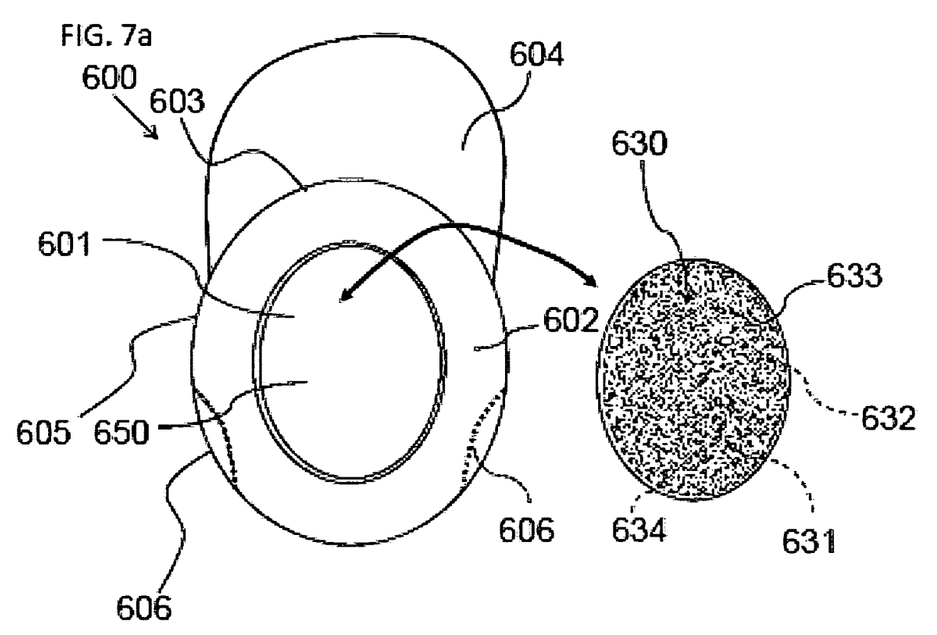
FIG. 7a illustrates a plane view of another embodiment of a hat constructed in accordance with the subject invention wherein the cooling zone is removable.
Figure 7B:
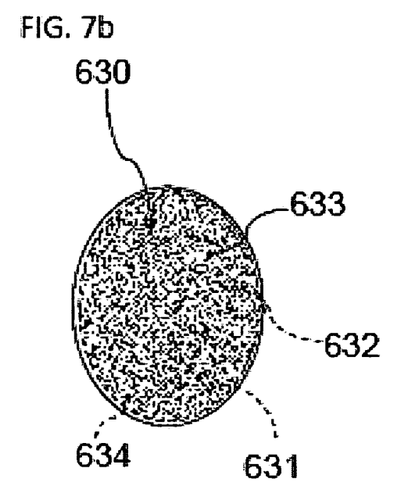
FIG. 7b illustrates a top plane view of the removed cooling zone.
Figure 7C:
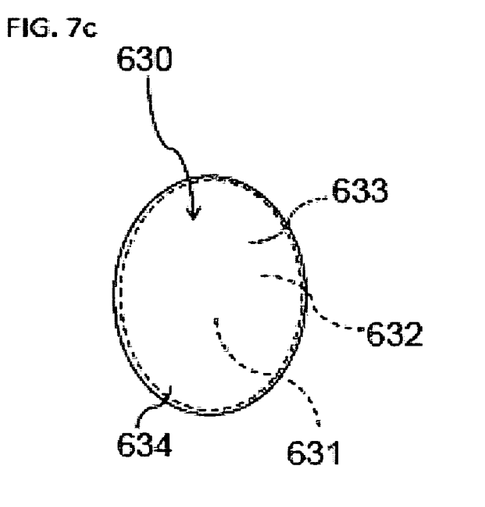
FIG. 7c illustrates a bottom plane view of the removed cooling zone.

FIGS. 7a-7c illustrate plane views of another embodiment of a hat constructed in accordance with the subject invention wherein the cooling zone is removable. FIG. 7a illustrates the assembled hat; FIG. 7b illustrates a top plane view of the removed cooling zone; and FIG. 7c illustrates a bottom plane view of the removed cooling zone. Although the hat is shown, the removable features may be incorporated into the shirt construct of the subject invention. The hat is shown generally at 600 and includes a top portion 601, side portions 602 and a front portion 603 having a visor member 604 attached thereto. The side portions 602 have a lower rim 605 circumferentially surrounding the bottom of the hat 600. Securement means is integrated within the side portions 602. Additionally, two ear members 606 are integrated within the lower rim 605 of the side portions 602. At least a portion of the hat comprises ultraviolet properties. Moreover, at least a portion of the hat 600 comprises a cooling zone 630. The cooling zone 630 further comprises of a plurality of cooling crystals/hydrophilic material 631 formed in a cavity 632 located. In the embodiment shown the hat the cooling zone 630 is removable. It is preferably composed of an external layer 633 and a bottom layer 634 forming the internal cavity 632 containing hydrophilic material 631/cooling crystals. The bottom layer 634 preferably includes attachment means, such as hook and loop fasteners such as that commonly sold under the trade name VELCRO, and is appointed to be removably attached to the top portion 601 of the hat by way of mating hook and loop fasteners. Although herein the top portion 601 includes the attachment mating fasteners in a segment 650, the segment 650 may be located in another location on the hat. Additionally, the hat may include more than one segments 650 each appointed to receive a cooling zone 630 removably thereon. Preferably, the bottom layer 634/innermost layer (resting against the dog) of the cavity 632 is composed of an absorbent cotton material while the external layer 633/outer layer is composed of the rash guard material. In this manner the cooling zone can be removed and soaked in water, without the need to soak the whole hat/shirt in water. Once the cooling zone 630 is saturated with cold water it can be wringed and placed onto the segment 650 and attached thereto for cooling and wear.

The article of clothing for a pet as disclosed herein can be modified in numerous ways without departing from the scope of the invention. Optional materials, sizes, and colors can be utilized.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:
1. An article of clothing for a pet comprising:
 a. a top portion, bottom portion, and side portions constructed to form a one-piece pullover tubular member having an opened torso end;

b. two leg members integrated within said tubular member;

c. a collar member integrated within said tubular member located opposite from said opened torso end;

d. at least a portion of said tubular member comprising ultraviolet properties;

e. at least a portion of said tubular member comprising at least three cooling zones, said cooling zones each further being comprised of a plurality of cooling crystals formed in a cavity located within said tubular member;

f. said cooling zones being located in said collar member wherein said cooling zone in said collar member extends circumferentially entirely around said collar member, at centralized under-leg areas between said tubular member and said two leg members, and in said bottom portion of said tubular member, said cooling zone abutting said collar member and said cooling zone extending from said collar member to said torso end;

g. wherein said cooling zone includes an external layer and a bottom layer and contains said cooling crystals, wherein said bottom layer of said cooling zone is composed of a fibrous material adapted to absorb water and is appointed to rest flush against an animal's body, wherein said external layer of said cooling zone is composed of a rash guard material, and wherein said cooling zones containing said cooling crystals are continuously formed in said collar member and said bottom portion so that said cooling zones are connected continuous cooling zones;

wherein said article of clothing is adapted to be soaked in water so that said fibrous material and said cooling crystals absorb said water and said rash guard material is appointed to be wrung-out to remove most of said water, and wherein said article of clothing is adapted to keep said pet cool and comfortable to mitigate heat exhaustion.

2. The article of clothing for a pet as recited by claim 1, wherein said cooling zone is located on said top portion of said tubular member and is appointed to cool a top torso of an animal.

3. The article of clothing for a pet as recited by claim 1, wherein said cooling zone is appointed to be removably attached to said tubular member by way of attachment means.

4. The article of clothing for a pet as recited by claim 1, wherein said two leg members include a cooling zone.

5. The article of clothing for a pet as recited by claim 1, wherein said article is composed of fabric or/fabric combinations classified as rash guard type materials, including spandex, nylon, polyester, Lycra and polypropylene material constructs, or combinations thereof.

6. The article of clothing for a pet as recited by claim 1, wherein said fibrous material is a lightweight absorbent cotton.

* * * * *